(12) United States Patent
Cuberes-Altisent et al.

(10) Patent No.: US 8,138,186 B2
(45) Date of Patent: Mar. 20, 2012

(54) PYRAZOLE DERIVATIVES AS SIGMA RECEPTORS ANTAGONISTS

(75) Inventors: Rosa Cuberes-Altisent, Barcelona (ES); Joerg Holenz, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 298 days.

(21) Appl. No.: 12/281,246

(22) PCT Filed: Mar. 2, 2007

(86) PCT No.: PCT/EP2007/001827
§ 371 (c)(1),
(2), (4) Date: Jan. 29, 2009

(87) PCT Pub. No.: WO2007/098964
PCT Pub. Date: Sep. 7, 2007

(65) Prior Publication Data
US 2009/0227589 A1 Sep. 10, 2009

(30) Foreign Application Priority Data
Mar. 2, 2006 (EP) .................................. 06004288

(51) Int. Cl.
*A61K 31/5377* (2006.01)
*C07D 413/02* (2006.01)
(52) U.S. Cl. .................................. 514/237.2; 544/140
(58) Field of Classification Search ............. 514/237.2; 544/140
See application file for complete search history.

(56) References Cited

U.S. PATENT DOCUMENTS
6,525,059 B1 * 2/2003 Anantanarayan et al. .... 514/256

FOREIGN PATENT DOCUMENTS
| DE | 118 636 A1 | 3/1976 |
| DE | 118 637 A1 | 3/1976 |
| EP | 1634872 A | 3/2006 |
| WO | WO 9525733 A | 9/1995 |
| WO | WO 00 27394 | * 5/2000 ............. 514/406 |
| WO | WO 2006021462 A | 3/2006 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Golub et al. Science (1999), vol. 286 531-537.*
Lala et al. Cancer and Metastasis Reviews (1998), 17(1), 91-106.*
The International Search Report for PCT/EP2007/001827, dated Oct. 3, 2007.

* cited by examiner

*Primary Examiner* — Rebecca Anderson
*Assistant Examiner* — Samantha Shterengarts
(74) *Attorney, Agent, or Firm* — Heslin Rothenberg Farley & Mesiti P.C.; Andrew K. Gonsalves

(57) ABSTRACT

The present invention relates to compounds of formula (I), methods for their preparation, medicaments comprising these compounds as well their use in the manufacture of a medicament for the treatment of humans and animals.

22 Claims, No Drawings

PYRAZOLE DERIVATIVES AS SIGMA RECEPTORS ANTAGONISTS

FIELD OF THE INVENTION

The present invention relates to compounds having pharmacological activity towards the sigma (σ) receptor, and more particularly to some pyrazole derivatives, to processes of preparation of such compounds, to medicaments comprising them, and to their use in therapy and prophylaxis, in particular for the treatment of psychosis.

BACKGROUND OF THE INVENTION

The search for new therapeutic agents has been greatly aided in recent years by better understanding of the structure of proteins and other biomolecules associated with target diseases. One important class of these proteins is the sigma (σ) receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews*, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol.

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma (σ-2) site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.,* 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Sci.,* 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

International Patent Application WO 91/09594 generically describes a broad class of sigma receptor ligands some of which are 4-phenylpiperidine, -tetrahydro-pyridine or -piperazine compounds having an optionally substituted aryl or heteroaryl, alkyl, alkenyl, alkynyl, alkoxy or alkoxyalkyl substituent on the ring N-atom. The terms aryl and heteroaryl are defined by mention of a number of such substituents.

European patent application EP 0 414 289 A1 generically discloses a class of 1,2,3,4-tetrahydro-spiro[naphthalene-1,4'-piperidine] and 1,4-dihydro-spiro[naphthalene-1,4'-piperidine] derivatives substituted at the piperidine N-atom with a hydrocarbon group alleged to have selective sigma receptor antagonistic activity. The term hydrocarbon, as defined in said patent, covers all possible straight chained, cyclic, heterocyclic, etc. groups. However, only compounds having benzyl, phenethyl, cycloalkylmethyl, furyl- or thienylmethyl or lower alkyl or alkenyl as the hydrocarbon substituent at the piperidine nitrogen atom are specifically disclosed. The compounds are stated to displace tritiated di-tolyl guanidine (DTG) from sigma sites with potencies better than 200 nM. 1-benzyl-1,2,3,4-tetrahydro-spiro [naphthalene-1,4'-piperidine] is mentioned as a particularly preferred compound.

European patent application EP 0 445 974 A2 generically describes the corresponding spiro[indane-1,4'-piperidine] and spiro[benzocycloheptene-5,4'-piperidine] derivatives. Again the compounds are only stated to displace tritiated di-tolyl guanidine (DTG) from sigma sites with potencies better than 200 nM.

European patent Application EPO 431 943 A relates to a further extremely broad class of spiropiperidine compounds substituted at the piperidine N-atom and claimed to be useful as antiarrhythmics and for impaired cardiac pump function. The said application exemplifies several compounds, the majority of which contain an oxo and/or a sulfonylamino substituent in the spiro cyclic ring system. Of the remainder compounds, the main part has another polar substituent attached to the spiro nucleus and/or they have some polar substituents in the substituent on the piperidine N-atom. No suggestion or indication of effect of the compounds on the sigma receptor is given.

Patent applications EP 518 805 A and WO 02/102387 describe sigma receptor ligands having piperidine or spiropiperidine structures.

With regard to the chemical structure of the compounds described in the present patent application, there are some documents in the prior art which disclose pyrazole derivatives characterized, among other things, for being substituted by amino alkoxy groups in different positions of the pyrazole group.

U.S. Pat. No. 4,337,263 discloses 1-aryl-4-arylsulphonyl-3-amino propoxy-1H-pyrazoles, wherein the amino group can be constituted by an N-cycle group as morpholine, piperidine or pyrrolidine group. They are used as hypolipemiant or hypocholesteroleminant agents.

Patent FR 2301250 describes similar compounds as those mentioned above, such as 1,4-diaryl-3-aminoalcoxy pyrazoles, wherein the amino group comprises pyrrolidine, piperidine, hydroxypiperidine, morpholine or piperazine derivatives.

Patent Application US2003/0144309 refers to pyrazoles with their 3 position substituted by a dimethylaminoethoxy group and present in their 4 position a pirimidine group. They are used as inhibitors of JNK3, Lck or Src kinase activity.

International patent Application WO 02/092573 describes substituted pyrazole compounds as inhibitors of SRC and other protein kinases.

International patent Application WO 2004/017961 discloses pyrazole compounds wherein the 3 position is substituted by an alcoxy group directly bounded to a cyclic amide, which are used for therapeutically treating and/or preventing a sex hormone related condition in a patient.

U.S. Pat. No. 6,492,529 describes pyrazole derivatives which are used for the treatment of inflammatory diseases. These compounds present in the 5 position a urea group, linked in some cases to a morpholine ethoxy group.

International patent Application WO 04/016592 refers to pyrazole compounds for inhibiting protein prenylation which comprises in the 5 position, among others, an alcoxy group directly bonded to a cyclic amide.

However, none of these documents suggests the effect of these compounds on the sigma receptor.

There is still a need to find compounds that have pharmacological activity towards the sigma receptor, being both effective and selective, and having good "drugability" properties, i.e. good pharmaceutical properties related to administration, distribution, metabolism and excretion.

SUMMARY OF THE INVENTION

We have now found a family of structurally distinct pyrazol derivatives which are particularly selective inhibitors of the sigma receptor. The compounds present a pyrazol group which are characterized by the substitution at position 3 by an alkoxy group directly bound to a nitrogen.

In one aspect the invention is directed to a compound of the formula (I):

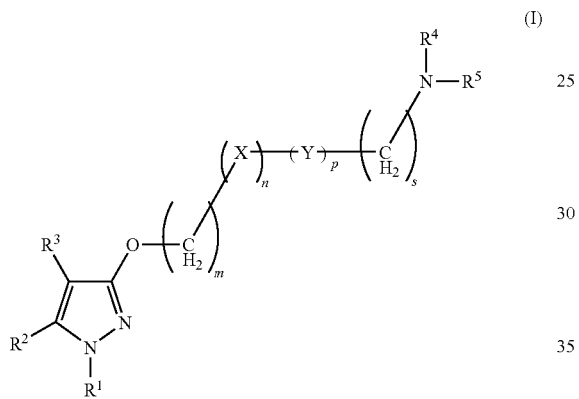

wherein $R^1$ represents a hydrogen atom; F; Cl; Br; I; $CF_3$; OH; SH; $NH_2$; CN; an unbranched or branched, saturated or unsaturated, optionally at least mono-substituted $C_{2-6}$ aliphatic group; an unbranched or branched, saturated or unsaturated, optionally at least mono-substituted alkoxy radical; a saturated or unsaturated, optionally at least mono-substituted, optionally at least one heteroatom as ring member containing cycloalkyl group, which may be condensed with an optionally at least mono-substituted mono- or polycyclic ring system; a branched or unbranched, optionally at least one heteroatom as ring member containing alkyl-cycloalkyl group in which the cycloalkyl group is optionally at least mono-substituted; an optionally at least mono-substituted aryl group which may be condensed with an optionally at least mono-substituted mono- or polycyclic ring system; an optionally at least mono-substituted heteroaryl group which may be condensed with an optionally at least mono-substituted mono- or polycyclic ring system; a branched or unbranched alkyl-aryl group in which the aryl group is optionally at least mono-substituted and/or condensed with a mono- or polycyclic ring system; a branched or unbranched alkyl-heteroaryl group in which the heteroaryl group is optionally at least mono-substituted and/or condensed with a mono- or polycyclic ring system; a (C=O)—$R^7$ group; a (C=O)—O—$R^8$ group; a (S=$O_2$)—$R^9$ group; or a (C=O)—$NR^{10}R^{11}$ group;

$R^2$ and $R^3$ identical or different, represent a hydrogen atom; F; Cl; Br; I; $CF_3$; OH; SH; $NH_2$; CN; an unbranched or branched, saturated or unsaturated, optionally at least mono-substituted aliphatic group; an unbranched or branched, saturated or unsaturated, optionally at least mono-substituted alkoxy radical; a saturated or unsaturated, optionally at least mono-substituted, optionally at least one heteroatom as ring member containing cycloalkyl group, which may be condensed with an optionally at least mono-substituted mono- or polycyclic ring system; a branched or unbranched, optionally at least one heteroatom as ring member containing alkyl-cycloalkyl group in which the cycloalkyl group is optionally at least mono-substituted; an optionally at least mono-substituted aryl group which may be condensed with an optionally at least mono-substituted mono- or polycyclic ring system; an optionally at least mono-substituted heteroaryl group which may be condensed with an optionally at least mono-substituted mono- or polycyclic ring system; a branched or unbranched alkyl-aryl group in which the aryl group is optionally at least mono-substituted and/or condensed with a mono- or polycyclic ring system; a branched or unbranched alkyl-heteroaryl group in which the heteroaryl group is optionally at least mono-substituted and/or condensed with a mono- or polycyclic ring system; a (C=O)—$R^7$ group; a (C=O)—O—$R^8$ group; a (S=$O_2$)—$R^9$ group; or a (C=O)—$NR^{10}R^{11}$ group;

$R^4$ and $R^5$ identical or different, represent a hydrogen atom; an unbranched or branched, saturated or unsaturated, optionally at least mono-substituted aliphatic group; an unbranched or branched, optionally at least mono-substituted alkoxy radical; a saturated or unsaturated, optionally at least one heteroatom as ring member containing cycloalkyl group, which may be condensed with an optionally at least mono-substituted mono- or polycyclic ring system; a branched or unbranched, optionally at least one heteroatom as ring member containing alkyl-cycloalkyl group in which the cycloalkyl group may be optionally at least mono-substituted; an optionally at least mono-substituted aryl group which may be condensed with an optionally at least mono-substituted mono- or polycyclic ring system; an optionally at least mono-substituted heteroaryl group which may be condensed with an optionally at least mono-substituted mono- or polycyclic ring system; a branched or unbranched alkyl-aryl group in which the aryl group is optionally at least mono-substituted and/or condensed with a mono- or polycyclic ring system; a branched or unbranched alkyl-heteroaryl group in which the heteroaryl group is optionally at least mono-substituted and/or condensed with a mono- or polycyclic ring system; a (C=O)—$R^7$ group; a (C=O)—O—$R^8$ group; a (S=$O_2$)—$R^9$ group; or a (C=O)—$NR^{10}R^{11}$ group;

or form together with the bridging nitrogen atom an optionally at least mono-substituted heterocyclyl group which is optionally condensed with an optionally at least mono-substituted mono- or polycyclic ring system;

X represents an oxygen atom; a CH—$R^{12}$ group with $R^{12}$ being —$CH_3$, SH, OH, $NH_2$, $CF_3$ group; Cl, F, Br, I, or CN;

Y represents a (S=$O_2$) group;

m is selected from 1, 2, 3 or 4;

n is selected from 0 or 1;

p is selected from 0 or 1;
s is selected from 1, 2, 3 or 4;
and n plus p is 1;
$R^7$, $R^8$, $R^9$, $R^{10}$ and $R^{11}$, identical or different, represent a hydrogen atom; an unbranched or branched, saturated or unsaturated, optionally at least mono-substituted $C_{1-6}$ aliphatic group; a branched or unbranched optionally at least mono-substituted $C_{1-6}$ alkoxy radical; a saturated or unsaturated, optionally at least mono-substituted, optionally at least one heteroatom as ring member containing cycloalkyl group; a branched or unbranched, optionally at least mono-substituted, optionally at least one heteroatom as ring member containing $C_{1-6}$ alkyl-cycloalkyl group; an optionally at least mono-substituted aryl group; an optionally at least mono-substituted heteroaryl group; a branched or unbranched, optionally at least mono-substituted $C_{1-6}$ alkyl-aryl; a branched or unbranched, optionally at least mono-substituted $C_{1-6}$ alkyl-heteroaryl group;
with the condition that —$(CH_2)_m$—$(X)_n$—$(Y)_p$—$(CH_2)_s$— may not represent a linear-$(CH_2)$—$(CH_2)$—$(CH_2)$— group or a linear —$(CH_2)$—$(CH_2)$—$(CH_2)$—$(CH_2)$— group;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one embodiment the following proviso applies:
with the proviso that if n is 1 and p is 0 and X represents a CH—$R^{12}$ group with $R^{12}$ being OH, $R^4$ and $R^5$ form together with the bridging nitrogen atom an optionally at least mono-substituted heterocyclyl group which is optionally condensed with an optionally at least mono-substituted mono- or polycyclic ring system.

In another embodiment the following proviso applies:
with the proviso that if n is 1 and p is 0 and X represents a CH—$R^{12}$ group with $R^{12}$ being OH, $R^3$ is hydrogen.

In another embodiment the following proviso applies:
with the proviso that the following compounds are excluded:
3-(3'-t-butylamino-2'-hydroxy-propoxy)-1-benzyl-pyrazol;
3-(3'-isopropylamino-2'-hydroxy-propoxy)-pyrazol;
3-(3'-isopropylamino-2'-hydroxy-propoxy)-1-isopropyl-pyrazol;
3-(3'-Isopropylamino-2'-hydroxy-propoxy)-1-(4-isopropyl-benzyl)-pyrazol;
3-(3'-Isopropylamino-2'-hydroxy-propoxy)-1-phenyl-pyrazol;
3-(3'-Isopropylamino-2'-hydroxy-propoxy)-1-cyclo-hexyl-pyrazol;
3-(3'-Isopropylamino-2'-hydroxy-propoxy)-1-furfuryl-pyrazol.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

The term "condensed" according to the present invention means that a ring or ring-system is attached to another ring or ring-system, whereby the terms "annulated" or "annelated" are also used by those skilled in the art to designate this kind of attachment.

The term "ring system" according to the present invention refers to ring systems comprises saturated, unsaturated or aromatic carbocyclic ring systems which contain optionally at least one heteroatom as ring member and which are optionally at least mono-substituted. Said ring systems may be condensed to other carbocyclic ring systems such as aryl groups, naphtyl groups, heteroaryl groups, cycloalkyl groups, etc.

Cycloalkyl radicals, as referred to in the present invention, are understood as meaning saturated and unsaturated (but not aromatic), cyclic hydrocarbons, which can optionally be unsubstituted, mono- or polysubstituted. In these radicals, for example $C_{3-4}$-cycloalkyl represents $C_3$- or $C_4$-cycloalkyl, $C_{3-5}$-cycloalkyl represents $C_3$-, $C_4$- or $C_5$-cycloalkyl, etc. With respect to cycloalkyl, the term also includes saturated cycloalkyls in which optionally at least one carbon atom may be replaced by a heteroatom, preferably S, N, P or O. However, mono- or polyunsaturated, preferably monounsaturated, cycloalkyls without a heteroatom in the ring also in particular fall under the term cycloalkyl as long as the cycloalkyl is not an aromatic system.

Examples for cycloalkyl radicals preferably include but are not restricted to cyclopropyl, 2-methylcyclopropyl, cyclopropylmethyl, cyclobutyl, cyclopentyl, cyclopentylmethyl, cyclohexyl, cycloheptyl, cyclooctyl, acetyl, tert-butyl, adamantyl, pyrroline, pyrrolidine, pyrrolidineone, pyrazoline, pyrazolinone, oxopyrazolinone, aziridine, acetidine, tetrahydropyrrole, oxirane, oxetane, dioxetane, tetrahydrofurane, dioxane, dioxolane, oxathiolane, oxazolidine, thiirane, thietane, thiolane, thiane, thiazolidine, piperidine, piperazine or morpholine.

Cycloalkyl radicals, as defined in the present invention may optionally be mono- or polysubstituted by F, Cl, Br, I, $NH_2$, SH, OH, $SO_2$, $CF_3$, carboxy, amido, cyano, carbamyl, nitro, —$SO_2NH_2$, $C_{1-6}$ alkyl or $C_{1-6}$-alkoxy.

Aliphatic radicals/groups, as referred to in the present invention, are optionally mono- or polysubstituted and may be branched or unbranched, saturated or unsaturated. Unsaturated aliphatic groups, as defined in the present invention, include alkyl, alkenyl and alkinyl radicals. Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl, n-heptyl, n-octyl, n-nonyl and n-decyl. Preferred substituents for aliphatic radicals, according to the present invention, are F, Cl, Br, I, $NH_2$, SH, OH, $SO_2$, $CF_3$, carboxy, amido, cyano, carbamyl, nitro, phenyl, benzyl, —$SO_2NH_2$, $C_{1-6}$ alkyl and/or $C_{1-6}$-alkoxy.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—; $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—; $(CH_2)_{4-5}$ is to be understood as meaning —CH$_2$—CH$_2$—CH$_2$—CH$_2$— and —CH$_2$—CH$_2$—CH$_2$—CH$_2$—CH$_2$—, etc.

An aryl radical, as referred to in the present invention, is understood as meaning ring systems with at least one aromatic ring but without heteroatoms even in only one of the rings. These aryl radicals may optionally be mono- or polysubstituted with for example F, Cl, Br, I, NH$_2$, SH, OH, SO$_2$, CF$_3$, carboxy, amido, cyano, carbamyl, nitro, phenyl, benzyl, —SO$_2$NH$_2$, C$_{1-6}$ alkyl or C$_{1-6}$-alkoxy. Preferred examples of aryl radicals include but are not restricted to phenyl, naphthyl, fluoranthenyl, fluorenyl, tetralinyl or indanyl or anthracenyl radicals, which may optionally be mono- or polysubstituted.

A heteroaryl radical is understood as meaning heterocyclic ring systems which have at least one aromatic ring and may optionally contain one or more heteroatoms from the group consisting of nitrogen, oxygen and/or sulfur and may optionally be unsubstituted, mono- or polysubstituted by for example F, Cl, Br, I, NH$_2$, SH, OH, SO$_2$, CF$_3$, oxo, carboxy, amido, cyano, carbamyl, nitro, phenyl, benzyl, —SO$_2$NH$_2$, C$_{1-6}$ alkyl or C$_{1-6}$-alkoxy. Preferred examples of heteroaryls include but are not restricted to furan, benzofuran, thiophene, benzothiophene, pyrrole, pyridine, pyrimidine, pyridazine, pyrazine, quinoline, isoquinoline, phthalazine, benzo-1,2,5-thiadiazole, benzothiazole, indole, benzotriazole, benzodioxolane, benzodioxane, benzimidzole, carbazole and quinazoline.

The term "heterocyclyl" refers to a stable 3- to 15 membered, saturated, unsaturated and/or aromatic ring radical, consisting of at least 3 carbon atoms which can be replaced by at least one heteroatom, preferably nitrogen, oxygen, and sulfur. Heterocyclic radicals may be monocyclic or polycyclic ring systems which, including fused ring systems. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc. Said heterocyclic groups may be optionally fully or partly saturated or aromatic and are optionally, unless otherwise stated, at least mono-substituted by one or more substituents independently selected from the group consisting of F, Cl, Br, I, NH$_2$, SH, OH, SO$_2$, CF$_3$, oxo, carboxy, amido, cyano, carbamyl, nitro, phenyl, benzyl, —SO$_2$NH$_2$, C$_{1-6}$ alkyl or C$_{1-6}$-alkoxy.

Substituted alkyl-cycloalkyl, alkyl-aryl and alkyl-heteroaryl groups are to be understood as being substituted on the alkyl and/or the cycloalkyl, aryl or heteroaryl group. For example, an optionally substituted alkyl-aryl group means optional substitution of either the alkyl group, the aryl group or both the alkyl and the aryl group. Preferably, these groups are optionally mono- or polysubstituted by F, Cl, Br, I, NH$_2$, SH, OH, SO$_2$, CF$_3$, oxo, carboxy, amido, cyano, carbamyl, nitro, phenyl, benzyl, —SO$_2$NH$_2$, C$_{1-6}$ alkyl or C$_{1-6}$-alkoxy.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic—especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid— as an anion with at least one, preferably inorganic, cation which is physiologically tolerated—especially if used on humans and/or mammals. The salts of the alkali metals and alkaline earth metals are particularly preferred, and also those with NH$_4$, but in particular (mono)- or (di)sodium, (mono)- or (di)potassium, magnesium or calcium salts.

These physiologically acceptable salts can also be formed with anions or acids in the context of this invention is understood as meaning salts of at least one of the compounds used according to the invention—usually protonated, for example on the nitrogen—as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

The compounds of the invention may be in crystalline form either as free compounds or as solvates and it is intended that both forms are within the scope of the present invention. Methods of solvation are generally known within the art. Suitable solvates are pharmaceutically acceptable solvates. In a particular embodiment the solvate is a hydrate.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or, or of its salts, solvates or prodrugs.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon or $^{15}$N-enriched nitrogen are within the scope of this invention.

The term "pharmacological tool" refers to the property of compounds of the invention through which they are particularly selective ligands for Sigma receptors which implies that compound of formula (I), described in this invention, can be used as a model for testing other compounds as sigma ligands, ex. a radiactive ligands being replaced, and can also be used for modeling physiological actions related to sigma receptors.

Preferred are compounds of general formula (I) given above,
wherein

- $R^1$ represent a hydrogen atom; F; Cl; Br; I; $CF_3$; OH; SH; $NH_2$; CN; an unbranched or branched $C_{2-6}$ alkyl group which is optionally at least mono-substituted with substituents independently selected from the group consisting of F, Cl, Br, I, $NH_2$, SH, OH, $SO_2$, or $CF_3$; an unbranched or branched, alkoxy radical which is optionally substituted with substituents independently selected from the group consisting of F, Cl, Br, I, $NH_2$, SH, OH, $SO_2$, or $CF_3$; a saturated or unsaturated, optionally at least one heteroatom as ring member containing cycloalkyl group which is optionally at least mono-substituted with substituents independently selected from the group consisting of F. Cl, Br, I, $NH_2$, SH, OH, $SO_2$, or $CF_3$; a branched or unbranched, optionally at least one heteroatom as ring member containing alkyl-cycloalkyl group in which the cycloalkyl group is optionally at least mono-substituted with substituents independently selected from the group consisting of F, Cl, Br, I, $NH_2$, SH, OH, $SO_2$, or $CF_3$; an aryl group which is optionally at least mono-substituted with substituents independently selected from the group consisting of F, Cl, Br, I, $NH_2$, SH, OH, $SO_2$, or $CF_3$; a heteroaryl group which is optionally at least mono-substituted with substituents independently selected from the group consisting of F, Cl, Br, I, $NH_2$, SH, OH, $SO_2$, or $CF_3$; a branched or unbranched alkyl-aryl group which is optionally at least mono-substituted substituted with substituents independently selected from the group consisting of F, Cl, Br, I, $NH_2$, SH, OH, $SO_2$, or $CF_3$; a branched or unbranched alkyl-heteroaryl group which is optionally at least mono-substituted substituted with substituents independently selected from the group consisting of F, Cl, Br, I, $NH_2$, SH, OH, $SO_2$, or $CF_3$;
- $R^2$ represents a hydrogen atom; F; Cl; Br; I; $CF_3$; OH; SH; $NH_2$; CN; an unbranched or branched $C_{1-6}$ alkyl group which is optionally at least mono-substituted with substituents independently selected from the group consisting of F, Cl, Br, I, $NH_2$, SH, OH, $SO_2$, or $CF_3$; an unbranched or branched, alkoxy radical which is optionally substituted with substituents independently selected from the group consisting of F, Cl, Br, I, $NH_2$, SH, OH, $SO_2$, or $CF_3$; a saturated or unsaturated, optionally at least one heteroatom as ring member containing cycloalkyl group which is optionally at least mono-substituted with substituents independently selected from the group consisting of F, Cl, Br, I, $NH_2$, SH, OH, $SO_2$, or $CF_3$; a branched or unbranched, optionally at least one heteroatom as ring member containing alkyl-cycloalkyl group in which the cycloalkyl group is optionally at least mono-substituted with substituents independently selected from the group consisting of F, Cl, Br, I, $NH_2$, SH, OH, $SO_2$, or $CF_3$; an aryl group which is optionally at least mono-substituted with substituents independently selected from the group consisting of F, Cl, Br, I, $NH_2$, SH, OH, $SO_2$, or $CF_3$; a heteroaryl group which is optionally at least mono-substituted with substituents independently selected from the group consisting of F, Cl, Br, I, $NH_2$, SH, OH, $SO_2$, or $CF_3$; a branched or unbranched alkyl-aryl group which is optionally at least mono-substituted with substituents independently selected from the group consisting of F, Cl, Br, I, $NH_2$, SH, OH, $SO_2$, or $CF_3$; a branched or unbranched alkyl-heteroaryl group which is optionally at least mono-substituted with substituents independently selected from the group consisting of F, Cl, Br, I, $NH_2$, SH, OH, $SO_2$, or $CF_3$;
- $R^3$ represents a hydrogen atom; F; Cl; Br; I; $CF_3$; OH; SH; $NH_2$; CN; an unbranched or branched $C_{1-6}$ alkyl group which is optionally at least mono-substituted with substituents independently selected from the group consisting of F, Cl, Br, I, $NH_2$, SH, OH, $SO_2$, or $CF_3$; an unbranched or branched, alkoxy radical which is optionally substituted with substituents independently selected from the group consisting of F, Cl, Br, I, $NH_2$, SH, OH, $SO_2$, or $CF_3$; a saturated or unsaturated, optionally at least one heteroatom as ring member containing cycloalkyl group which is optionally at least mono-substituted with substituents independently selected from the group consisting of F, Cl, Br, I, $NH_2$, SH, OH, $SO_2$, or $CF_3$; a branched or unbranched, optionally at least one heteroatom as ring member containing alkyl-cycloalkyl group in which the cycloalkyl group is optionally at least mono-substituted with substituents independently selected from the group consisting of F, Cl, Br, I, $NH_2$, SH, OH, $SO_2$, or $CF_3$; an aryl group which is optionally at least mono-substituted with substituents independently selected from the group consisting of F; Cl; Br; I; $CF_3$; OH; SH; $NH_2$; CN; a heteroaryl group which is optionally at least mono-substituted with substituents independently selected from the group consisting of F, Cl, Br, I, $NH_2$, SH, OH, $SO_2$, or $CF_3$; a branched or unbranched alkyl-aryl group which is optionally at least mono-substituted with substituents independently selected from the group consisting of F, Cl, Br, I, $NH_2$, SH, OH, $SO_2$, or $CF_3$; a branched or unbranched alkyl-heteroaryl group which is optionally at least mono-substituted with substituents independently selected from the group consisting of F, Cl, Br, I, $NH_2$, SH, OH, $SO_2$, or $CF_3$;
- $R^4$ and $R^5$, identical or different, represent a hydrogen atom; an unbranched or branched, substituted $C_{1-6}$ alkyl group with substituents independently selected from the group consisting of F, Cl, Br, I, $NH_2$, SH, OH, $SO_2$, or $CF_3$; an unbranched or branched, alkoxy radical which is optionally substituted with substituents independently selected from the group consisting of F, Cl, Br, I, $NH_2$, SH, OH, $SO_2$, or $CF_3$; a saturated or unsaturated, optionally at least one heteroatom as ring member containing cycloalkyl group which is optionally at least mono-substituted with substituents independently selected from the group consisting of F, Cl, Br, I, $NH_2$, SH, OH, $SO_2$, or $CF_3$; a branched or unbranched, optionally at least one heteroatom as ring member containing alkyl-cycloalkyl group in which the cycloalkyl group is optionally at least mono-substituted with substituents independently selected from the group consisting of F, Cl, Br, I, $NH_2$, SH, OH, $SO_2$, or $CF_3$; an aryl group which is optionally at least mono-substituted with substituents independently selected from the group consisting of F, Cl, Br, I, $NH_2$, SH, OH, $SO_2$, or $CF_3$; a heteroaryl group which is optionally at least mono-substituted with substituents independently selected from the group consisting of F, Cl, Br, I, $NH_2$, SH, OH, $SO_2$, or $CF_3$; a branched or unbranched alkyl-aryl group which is optionally at least mono-substituted with substituents independently selected from the group consisting of F, Cl, Br, I, $NH_2$, SH, OH, $SO_2$, or $CF_3$; a branched or unbranched alkyl-heteroaryl group which is optionally at least mono-substituted with substituents independently selected from the group consisting of F, Cl, Br, I, $NH_2$, SH, OH, $SO_2$, or $CF_3$;
- or
- form together with the bridging nitrogen atom an optionally at least mono-substituted, at least one heteroatom as ring member containing cycloalkyl group;
- optionally in form of one of the stereoisomers, preferably enantiomers or diastereomers,
- a racemate or in form of a mixture of at least two of the stereoisomers, preferably enantiomers and/or diastereomers, in any mixing ratio, or a corresponding salt thereof, or a corresponding solvate thereof.

Another alternative embodiment of the present invention refers to compounds of formula (I) given above, wherein $R^4$ and $R^5$, identical or different, represent a hydrogen atom; an unbranched or branched, alkoxy radical which is optionally substituted with substituents independently selected from the group consisting of F, Cl, Br, I, $NH_2$, SH, OH, $SO_2$, or $CF_3$; a saturated or unsaturated, optionally at least one heteroatom as ring member containing cycloalkyl group which is optionally at least mono-substituted with substituents independently selected from the group consisting of F, Cl, Br, I, $NH_2$, SH, OH, $SO_2$, or $CF_3$; a branched or unbranched, optionally at least one heteroatom as ring member containing alkyl-cycloalkyl group in which the cycloalkyl group is optionally at least mono-substituted with substituents independently selected from the group consisting of F, Cl, Br, I, $NH_2$, SH, OH, $SO_2$, or $CF_3$; an aryl group which is optionally at least mono-substituted with substituents independently selected from the group consisting of F, Cl, Br, I, $NH_2$, SH, OH, $SO_2$, or $CF_3$; a heteroaryl group which is optionally at least mono-substituted with substituents independently selected from the group consisting of F, Cl, Br, I, $NH_2$, SH, OH, $SO_2$, or $CF_3$; a branched or unbranched alkyl-aryl group which is optionally at least mono-substituted with substituents independently selected from the group consisting of F, Cl, Br, I, $NH_2$, SH, OH, $SO_2$, or $CF_3$; a branched or unbranched alkyl-heteroaryl group which is optionally at least mono-substituted with substituents independently selected from the group consisting of F, Cl, Br, I, $NH_2$, SH, OH, $SO_2$, or $CF_3$;

or form together with the bridging nitrogen atom an optionally at least mono-substituted, at least one heteroatom as ring member containing cycloalkyl group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another alternative embodiment of the present invention refers to compounds of formula (I) given above, wherein $R^4$ and $R^5$ form together with the bridging nitrogen atom an optionally at least mono-substituted 5- or 6-membered ring selected from the group consisting of pyrrolidine, morpholine, piperidine or piperazine, preferably morpholine, pyrrolidine or piperidine.

Another alternative embodiment of the present invention refers to compounds of formula (I) given above, wherein m is selected from 1, 2, 3 or 4; preferably from 1 or 2.

Another alternative embodiment of the present invention refers to compounds of formula (I) given above, wherein n is selected from 0 or 1, preferably from 1.

Another alternative embodiment of the present invention refers to compounds of formula (I) given above, wherein p is selected from 0 or 1; preferably 1.

Another alternative embodiment of the present invention refers to compounds of formula (I) given above, wherein s is selected from 1, 2, 3 or 4; preferably 1 or 2.

Another alternative embodiment of the present invention refers to compounds of formula (I) given above, wherein X represents an oxygen atom; a CH—$R^{12}$ group with $R^{12}$ being —$CH_3$, SH, OH, $NH_2$, $CF_3$ group; Cl, F, Br, I, or CN;

Another alternative embodiment of the present invention refers to compounds of formula (I) given above, wherein X represents an oxygen atom or a CH—OH group;

Another alternative embodiment of the present invention refers to compounds of formula (I) given above, wherein Y represents an (S=$O_2$) group;

A preferred embodiment of the present invention refers to a compound of general formula (I) given above, wherein $R^1$ represents a hydrogen atom; F; Cl; Br; I; $CF_3$; OH; SH; $NH_2$; CN; an optionally, at least mono-substituted ethyl, propyl, n-propyl, i-propyl, tert-butyl, n-butyl, i-butyl, phenyl, benzyl, phenethyl, or naphtyl group with substituents independently selected from the group consisting of F, Cl, Br, I, $NH_2$, SH, OH, $SO_2$, or $CF_3$;

$R^2$ represents a hydrogen atom; an unbranched or branched, $C_{1-6}$ alkyl group which is optionally at least mono-substituted with substituents independently selected from the group consisting of F, Cl, Br, I, $NH_2$, SH, OH, $SO_2$, or $CF_3$; a branched or unbranched alkyl-aryl group selected from the group consisting of benzyl or phenethyl which is optionally at least mono-substituted with substituents independently selected from the group consisting of F, Cl, Br, I, $NH_2$, SH, OH, $SO_2$, or $CF_3$; a branched or unbranched alkyl-heteroaryl group which is optionally at least mono-substituted with substituents independently selected from the group consisting of F, Cl, Br, I, $NH_2$, SH, OH, $SO_2$, or $CF_3$;

$R^3$ represents a hydrogen atom; an unbranched or branched, $C_{1-6}$ alkyl group which is optionally at least mono-substituted with substituents independently selected from the group consisting of F, Cl, Br, I, $NH_2$, SH, OH, $SO_2$, or $CF_3$; a branched or unbranched alkyl-aryl group selected from the group consisting of benzyl or phenethyl which is optionally at least mono-substituted with substituents independently selected from the group consisting of F, Cl, Br, I, $NH_2$, SH, OH, $SO_2$, or $CF_3$; a branched or unbranched alkyl-heteroaryl group which is optionally at least mono-substituted with substituents independently selected from the group consisting of F, Cl, Br, I, $NH_2$, SH, OH, $SO_2$, or $CF_3$;

$R^4$ and $R^5$ form together with the bridging nitrogen atom an optionally at least mono-substituted, piperidine, morpholine, pyrrolidine or piperazine group which is optionally at least mono-substituted with substituents independently selected from the group consisting of F, Cl, Br, I, $NH_2$, SH, OH, $SO_2$, or $CF_3$;

X represents an oxygen atom or a CH—$R^{12}$ group with $R^{12}$ being OH;

Y represents a (S=$O_2$) group;

m is selected from 1 or 2;

n is selected from 0 or 1;

p is selected from 0 or 1;

s is selected from 1, 2, 3, or 4;

and n plus p is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Highly preferred are compounds of formula (I) given above, selected from the group consisting of:

1-(1-(3,4-dichlorophenyl)-1H-pyrazol-3-yloxy)-3-morpholinopropan-2-ol, 1-(1-(3,4-dichlorophenyl)-1H-pyrazol-3-yloxy)-3-(piperidin-1-yl)propan-2-ol, 1-(1-(3,4-dichlorophenyl)-1H-pyrazol-3-yloxy)-3-(pyrrolidin-1-yl)propan-2-ol,
1-(1-(3,4-dichlorophenyl)-1H-pyrazol-3-yloxy)-3-(4-methylpiperazin-1-yl)propan-2-ol,
2-(1-(3,4-dichlorophenyl)-1H-pyrazol-3-yloxy)ethyl 2-morpholine,
1-(2-(2-(1-(3,4-dichlorophenyl)-1H-pyrazol-3-yloxy)ethoxy)ethyl)piperidine,
4-(2-(2-(1-(3,4-dichlorophenyl)-1H-pyrazol-3-yloxy)ethoxy)ethyl)morpholine,
or any acceptable salt or solvate thereof.

Another aspect of the present invention relates to a process for the preparation of compounds of general formula (I) as described above.

The compounds of formula (I) defined above can be obtained by available synthetic procedures similar to those described in the U.S. Pat. No. 4,337,263 or FR 2 472 564. For example, they can be prepared by condensing a compound of formula (II):

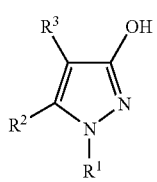

(II)

in which $R^1$, $R^2$ and $R^3$ are as defined above in formula (I), with a compound of formula (III):

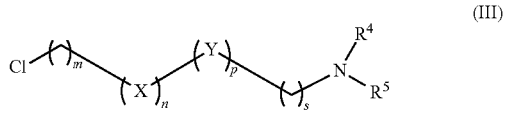

(III)

in which $R^4$, $R^5$, X, Y, m, n, p, and s are as defined above in formula (I).

The reaction of compounds of formulas (II) and (III) is preferably carried out at a temperature in the range of 60 to 120° C. in an aprotic solvent, but not limited to, such as dimethylformamide (DMF) in the presence of an inorganic base, such as $K_2CO_3$.

Alternatively, compounds of general formula (I) as described above can be obtained by condensing a compound of formula (II) as described above, in which $R^1$, $R^2$ and $R^3$ are as defined above in formula (I), with a compound of formula (IV):

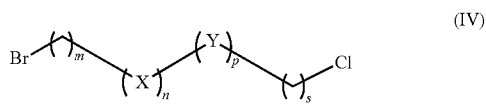

(IV)

in which X, Y, m, n, p, and s are as defined above in formula (I).

The reaction of compounds of formulas (II) and (IV) is preferably carried out in the presence of an organic or inorganic, e.g. $K_2CO_3$.

The intermediate compound (II) can also be prepared as described in the bibliography (see L. F. Tietze et al., Synthesis, (11), 1079-1080, 1993; F. Effenberger and W. Hartmann, Chem. Ber., 102(10), 3260-3267, 1969; both citations incorporated here by reference). It can also be prepared by conventional methods, as can be seen in the synthetic examples of the present patent application.

Compounds of formula (III) and (IV) are commercially available or can be prepared by conventional methods known to those ordinary skilled in the art.

A general for process for synthesizing compounds of general formula (I) as described above is given in scheme (I)

Scheme (I)

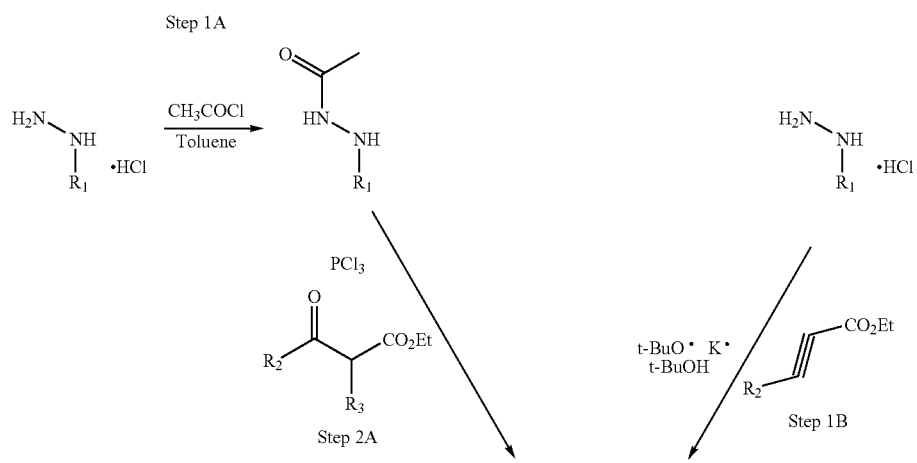

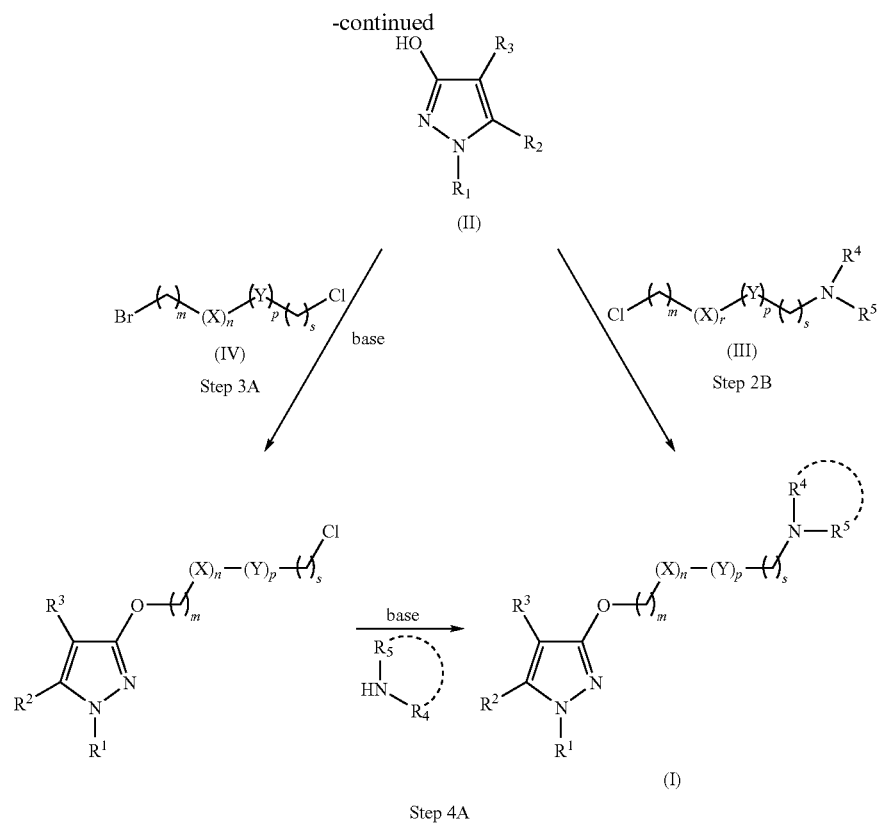

Compounds of general formula (I) as described above may be obtained by more than one route of synthesis, as described in scheme (I). Three of these alternative routes of synthesis are described more in detail in scheme 1A, 1B and 1C. These routes are to be understood as to form part of general scheme (I) and are therefore no restriction to the general process for obtaining compounds of general formula (I) as described above.

-continued

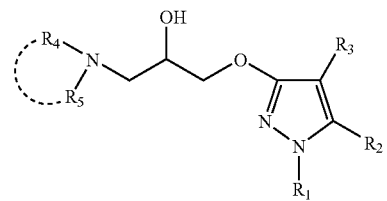

Scheme 1A

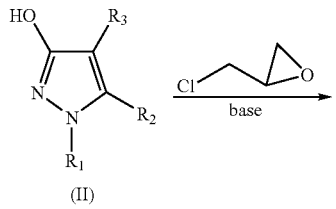

Scheme 1B

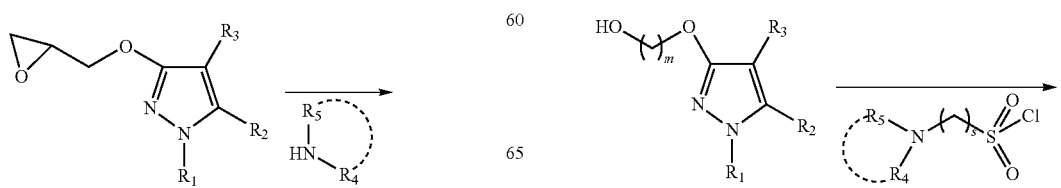

-continued

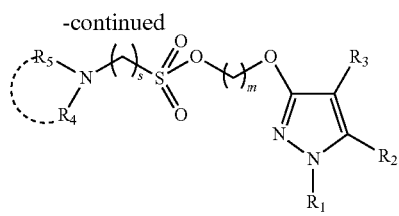

Scheme 1C

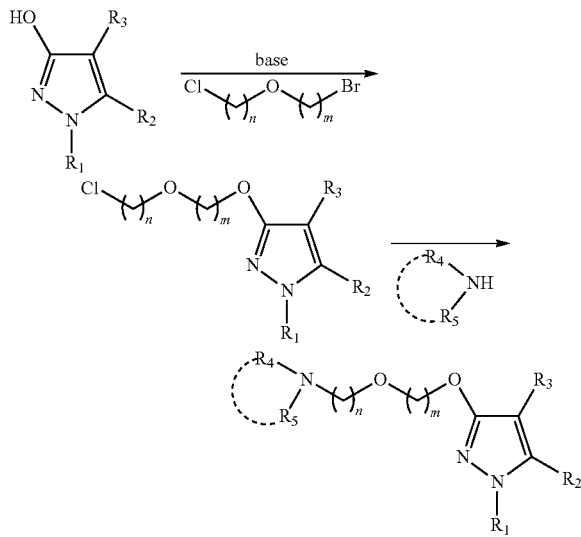

During the processes described above the protection of sensitive groups or of reagents may be necessary and/or desirable. The introduction of conventional protective groups as well as their removal may be performed by methods well-known to those skilled in the art.

If the compounds of general formula (I) themselves are obtained in form of a mixture of stereoisomers, particularly enantiomers or diastereomers, said mixtures may be separated by standard procedures known to those skilled in the art, e.g. chromatographic methods or fractionalized crystallization with chiral reagents. If there are chiral centers the compounds may be prepared in racemic form, or individual enantiomers may be prepared either by enantiospecific synthesis or by resolution.

Solvates, preferably hydrates, of the compounds of general formula (I), of corresponding stereoisomers, or of corresponding salts thereof may also be obtained by standard procedures known to those skilled in the art.

The purification and isolation of the inventive compounds of general formula (I), of a corresponding stereoisomer, or salt, or solvate or any intermediate thereof may, if required, be carried out by conventional methods known to those skilled in the art, e.g. chromatographic methods or recrystallization.

It has been found that the compounds of general formula (I) and given below, stereoisomers thereof, corresponding salts and corresponding solvates have high affinity to sigma receptors, i.e. they are selective ligands for the sigma receptor and act as modulators, e.g. antagonists, inverse agonists or agonists, on these receptors.

The compounds of general formula (I) given below, their stereoisomers, corresponding salts thereof and corresponding solvates are toxicologically acceptable and are therefore suitable as pharmaceutical active substances for the preparation of medicaments.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Another aspect of the present invention relates to a medicament comprising at least one compound of general formula (I) given above, said compound being optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof; or a prodrug thereof.

Another aspect of the present invention relates to a medicament comprising at least one compound of general formula (I) given above, said compound being optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an alternative embodiment of the present invention, the medicament comprises at least one compound of general formula (I), said compound being optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Another aspect of the invention is a medicament comprising at least one combination of compounds according to the invention and optionally one or more pharmaceutically acceptable excipients.

In an embodiment according to the invention the medicament is for the prophylaxis and/or treatment of one or more disorders selected from the group consisting of diarrhoea, lipoprotein disorders, migraine, obesity, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer or psychotic conditions, in particular depression, anxiety or schizophrenia; inflammation, or autoimmune diseases.

In an embodiment according to the invention the medicament is for the prophylaxis and/or treatment of one or more disorders selected from the group consisting of elevated triglyceride levels, chylomicronemia, dysbetalipoproteinemia, hyperlipoproteinemia, hyperlipidemia, mixed hyperlipidemia, hypercholesterolemia, lipoprotein disorders, hypertriglyceridemia, sporadic hypertriglyceridemia, inherited hypertriglyceridemia and/or dysbetalipoproteinemia.

In another embodiment according to the invention the medicament is for the prophylaxis and/or treatment of one or more disorders selected from the group consisting of pain, preferably neuropathic pain, inflammatory pain or other pain conditions involving allodynia and/or hyperalgesia.

Said medicament may also comprise any combination of one or more of the compounds of general formula (I) given above, stereoisomers thereof, physiologically acceptable salts thereof or physiologically acceptable solvates thereof.

Another aspect of the present invention is the use of at least one compound of general formula (I) given above as suitable active substances, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, and optionally one or more pharmaceutically acceptable excipients, for the preparation of a medicament for the modulation of sigma receptors, preferably for the prophylaxis and/or treatment of psychosis.

The medicament according to the present invention may be in any form suitable for the application to humans and/or animals, preferably humans including infants, children and adults and can be produced by standard procedures known to those skilled in the art. The composition of the medicament may vary depending on the route of administration.

The medicament of the present invention may for example be administered parentally in combination with conventional injectable liquid carriers, such as water or suitable alcohols. Conventional pharmaceutical excipients for injection, such as stabilizing agents, solubilizing agents, and buffers, may be included in such injectable compositions. These medicaments may for example be injected intramuscularly, intraperitoneally, or intravenously.

Solid oral compositions (which are preferred as are liquid ones) may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to the methods well known in normal pharmaceutical practice, in particular with an enteric coating.

The mentioned formulations will be prepared using standard methods such as those described or referred to in the Spanish and US Pharmacopeias and similar reference texts.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered forms suitable for reconstitution with water or other suitable liquid medium before use, for immediate or retarded release.

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

Another aspect of the present invention refers to a method for the prophylaxis and/or treatment of diarrhoea, lipoprotein disorders, migraine, obesity, elevated trigyceride levels, chylomicronemia, dysbetalipoproteinemia, hyperlipoproteinemia, hyperlipidemia, mixed hyperlipidemia, hypercholesterolemia, lipoprotein disorders, hypertriglyceridemia, sporadic hypertriglyceridemia, inherited hypertriglyceridemia and dysbetalipoproteinemia, arthritis, hypertension, arrhythmia, ulcer, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer or psychotic conditions, in particular depression, anxiety or schizophrenia; inflammation, or autoimmune diseases, the method comprising administering to the subject at least one compound of general formula (I) as described above and optionally at least one further active substance and/or optionally at least one auxiliary substance to the subject.

A preferred embodiment of the present invention refers to a method for the prophylaxis and/or treatment of elevated trigyceride levels, chylomicronemia, dysbetalipoproteinemia, hyperlipoproteinemia, hyperlipidemia, mixed hyperlipidemia, hypercholesterolemia, lipoprotein disorders, hypertriglyceridemia, sporadic hypertriglyceridemia, inherited hypertriglyceridemia and/or dysbetalipoproteinemia.

The present invention is illustrated below with the aid of examples. These illustrations are given solely by way of example and do not limit the general spirit of the present invention.

EXAMPLES

Example 1

Synthesis of 1-(1-(3,4-dichlorophenyl)-1H-pyrazol-3-yloxy)-3-morpholinopropan-2-ol oxalate 1) Scheme 1A-step 1. Synthesis of 1-(3,4-dichlorophenyl)-3-(oxiran-2-ylmethoxy)-1H-pyrazole

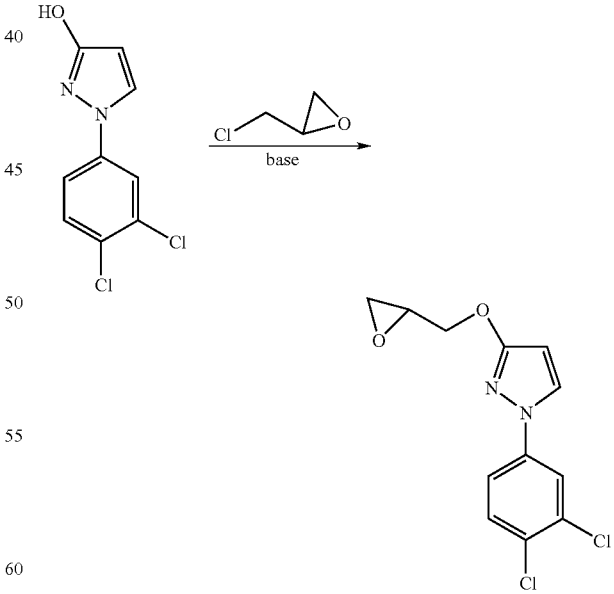

A mixture of 1-(3,4-dichlorophenyl)-1H-pyrazol-3-ol (0.2 g, 0.87 mmol; compound prepared in the same way as Example 1, Scheme 1-step 1B), 2-(chloromethyl)oxirane (0.1 g, 1.05 mmol), potassium carbonate (0.36 g, 2.62 mmol) and sodium iodide (0.13 g, 0.87 mmol) in dimethylformamide (6 ml) was warmed, with stirring, to 100° C. for 4 hrs. The solvent was evaporated to dryness in vacuo and residue partitioned between water and dichlorometane. The combined organic phases were dried over sodium sulphate, filtered and evaporated in vacuo to yield 0.24 g of 1-(3,4-dichlorophenyl)-3-(oxiran-2-ylmethoxy)-1H-pyrazole as a dark oil, used without further purification in next step of synthesis.

$^1$H-NMR (CDCl$_3$) δ ppm: 7.75 (d, J=2.4 Hz, 1H), 7.7 (d, J=2.6 Hz, 1H), 7.45 (d, J=8.8 Hz, 1H), 7.4 (dd, J=2.5 and 8.8 Hz, 1H), 5.95 (d, J=2.6 Hz, 1H), 4.55 (dd, J=3.1 and 11.7 Hz, 1H), 4.2 (dd, J=6.0 and 11.7 Hz, 1H), 3.4 (m, 1H), 2.9 (dd, J=5.0 and 9.1 Hz, 1H), 2.75 (dd, J=2.7 and 5.0 Hz, 1H).

2) Scheme 1A-step 2. Synthesis of 1-(1-(3,4-dichlorophenyl)-1H-pyrazol-3-yloxy)-3-morpholinopropan-2-ol

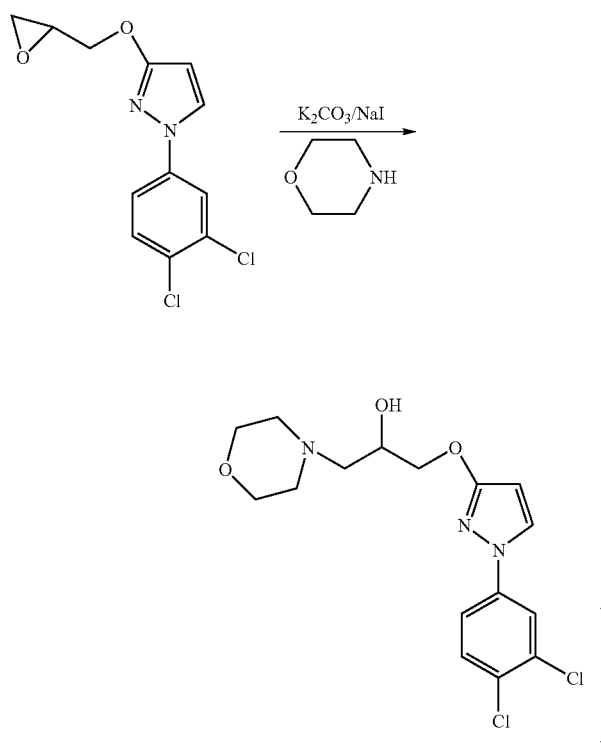

A mixture of 1-(3,4-dichlorophenyl)-3-(oxiran-2-ylmethoxy)-1H-pyrazole (0.23 g, 0.82 mmol), morpholine (72 mg, 0.82 mmol), potassium carbonate (0.34 g, 2.47 mmol) and sodium iodide (123 mg, 0.82 mmol) in dimethylformamide (6 ml) was refluxed 8 hrs and the solvent evaporated in vacuo. To the crude residue was added water and dichlorometane, the aqueous solution extracted several times with dichlorometane and the combined organic phases washed with water, dried over sodium sulphate, filtered and evaporated to dryness in vacuo. The crude dark oil obtained, 296 mg, was purified by column chromatography on silica gel (eluent: ethyl acetate/petroleum ether 1:1 to 1:0 and ethyl acetate/CH$_3$OH 9:1) yielding 114 mg of 1-(1-(3,4-dichlorophenyl)-1H-pyrazol-3-yloxy)-3-morpholinopropan-2-ol.

The salt with oxalic acid was prepared analogously to method described in Example 1, obtaining a white solid with m.p.=158-161° C.

$^1$H-NMR (DMSO-d$_6$) δ ppm: 8.45 (d, J=2.8 Hz, 1H), 8.0 (d, J=1.9 Hz, 1H), 7.7 (m, 2H), 6.1 (d, J=2.8 Hz, 1H), 4.2 (m, 1H), 4.1 (m, 2H), 3.6 (bm, 4H), 2.7 (m, 6H).

The following examples 2-4 were prepared with the same synthetic steps used in Example 1.

Example 2

1-(1-(3,4-dichlorophenyl)-1H-pyrazol-3-yloxy)-3-(piperidin-1-yl)propan-2-ol oxalate

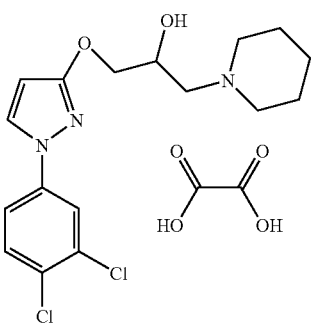

White solid. M.p.=116-119° C.

$^1$H-NMR (CD$_3$OD) δ ppm: 8.1 (d, J=2.6 Hz, 1H), 7.9 (d, J=2.2 Hz, 1H), 7.65 (dd, J=2.2 and 8.9 Hz, 1H), 7.6 (d, J=8.9 Hz, 1H), 6.0 (d, J=2.6 Hz, 1H), 4.5 (m, 1H), 4.3 (m, 2H), 3.4-3.2 (m, 6H), 1.9 (m, 4H), 1.7 (m, 2H).

Example 3

1-(1-(3,4-dichlorophenyl)-1H-pyrazol-3-yloxy)-3-(pyrrolidin-1-yl)propan-2-ol oxalate

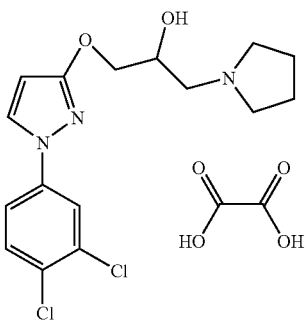

White solid. M.p.=123, 5-129° C.

¹H-NMR (CD₃OD) δ ppm: 8.1 (d, J=2.8 Hz, 1H), 7.9 (d, J=2.3 Hz, 1H), 7.65 (dd, J=2.3 and 8.9 Hz, 1H), 7.55 (d, J=8.9 Hz, 1H), 6.0 (d, J=2.8 Hz, 1H), 4.4-4.2 (m, 3H), 3.4-3.2 (m, 6H), 2.15 (m, 4H).

Example 4

1-(1-(3,4-dichlorophenyl)-1H-pyrazol-3-yloxy)-3-(4-methylpiperazin-1-yl)propan-2-ol dioxalate

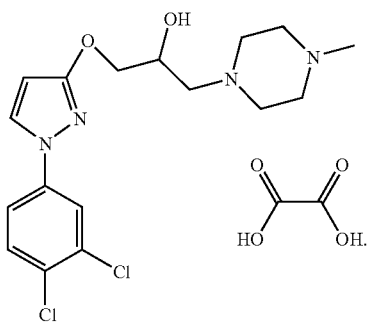

White solid. M.P.=189-192° C.
¹H-NMR (DMSO-d₆+TFA) δ ppm: 8.25 (d, J=2.5 Hz, 1H), 7.9 (bs, 1H), 7.6 (d, J=8.8 Hz, 1H), 7.5 (d, J=8.8 Hz, 1H), 5.95 (d, J=2.5 Hz, 1H), 4.3 (m, 1H), 4.2 (m, 2H), 3.5-3.3 (m+H₂O, 10H), 2.8 (s, 3H).

Example 5

Synthesis of 2-(1-(3,4-dichlorophenyl)-1H-pyrazol-3-yloxy)ethyl 2-morpholino ethane sulfonate 1) Scheme 1B-Step 1. Synthesis of 2-(1-(3,4-dichlorophenyl)-1H-pyrazol-3-yloxy)ethanol

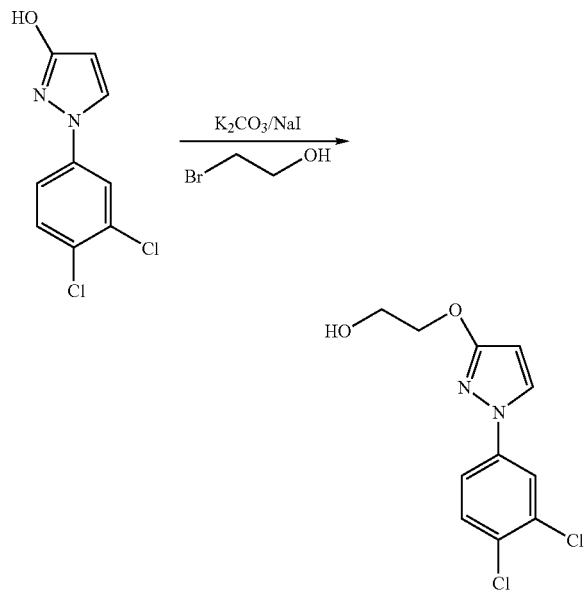

A mixture of 1-(3,4-dichlorophenyl)-1H-pyrazol-3-ol (238 mg, 1.04 mmol; compound prepared in the same way as Example 1, Scheme 1-step 1B), 2-bromoethanol (273 mg, 2.08 mmol), potassium carbonate (0.43 g, 3.12 mmol) and sodium iodide (0.16 g, 1.04 mmol) in dimethylformamide (5 ml) was warmed, under dry nitrogen atmosphere, with stirring, to 60° C. overnight. The solvent was evaporated to dryness in vacuo and residue partitioned between water and ethyl ether. The combined organic phases were washed with water and dried over sodium sulphate, filtered and evaporated in vacuo. The residue was stirred with petroleum ether at 45° C. and decanted for 3 times to yield, after drying, 258 mg of 2-(1-(3,4-dichlorophenyl)-1H-pyrazol-3-yloxy)ethanol which was used without further purification in the next step of synthesis ¹H-NMR (CDCl₃) δ ppm: 7.7 (d, J=2.3 Hz, 1H), 7.65 (d, J=2.7 Hz, 1H), 7.45 (d, J=8.7 Hz, 1H), 7.4 (dd, J=2.3 and 8.7 Hz, 1H), 5.95 (d, J=2.7 Hz, 1H), 4.4 (m, 2H), 4.0 (m, 2H).

2) Scheme 1B-Step 2. Synthesis of 2-(1-(3,4-dichlorophenyl)-1H-pyrazol-3-yloxy)ethyl 2-morpholinoethanesulfonate

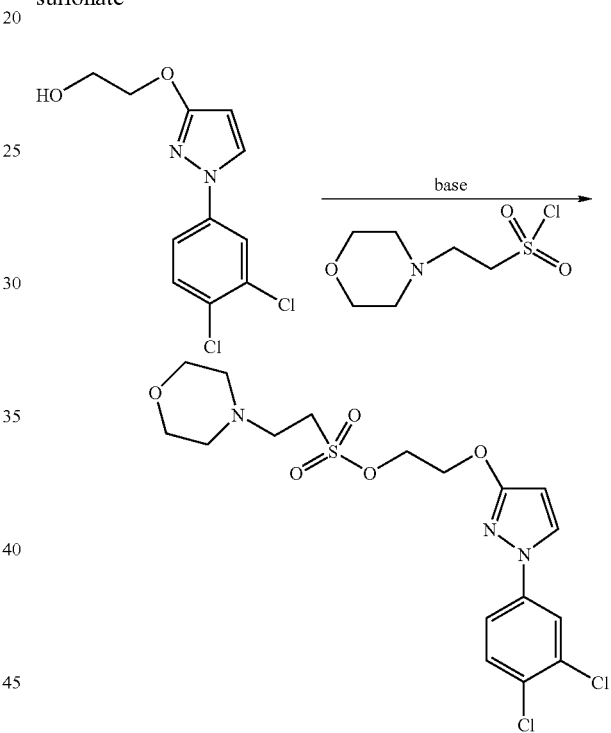

To a solution of 2-(1-(3,4-dichlorophenyl)-1H-pyrazol-3-yloxy)ethanol (154 mg, 0.53 mmol) and tryethylamine (0.22 ml, 1.58 mmol) in dichlorometane (9 ml) was added a solution of 2-morpholinoethanesulfonyl chloride (prepared from 0.69 mmol of 2-morpholinoethanesulfonic acid and 1.14 ml of oxalyl dichloride in dichlorometane at 0° C.) and the final mixture was stirred at room temperature overnight. Water was added, the organic phase separated and the aqueous phase extracted with more dichlorometane. The combined organic phases were washed with saturated aqueous solution of NaHCO₃ and water, and after drying over sodium sulphate, filtered and evaporated to dryness yielding 222 mg of crude compound. After column chromatography purification (silica gel, eluent: petroleum ether/ethyl acetate 8:2), 94 mg of 2-(1-(3,4-dichlorophenyl)-1H-pyrazol-3-yloxy)ethyl 2-morpholinoethanesulfonate as a solid was obtained, with a m.p.=120-122° C. after crystallization in acetone-petroleum ether.

¹H-NMR (DMSO-d₆) δ ppm: 8.45 (d, J=2.6 Hz, 1H), 8.0 (d, J=2.2 Hz, 1H), 7.7 (m, 2H), 6.1 (d, J=2.6 Hz, 1H), 4.55 (t, J=3.2 Hz, 2H), 4.45 (t, J=3.5 Hz, 2H), 3.6-3.5 (m, 6H), 2.65 (t, J=7.6 Hz, 2H), 2.35 (t, J=4.4 Hz, 4H).

Example 6

Synthesis of 1-(2-(2-(1-(3,4-dichlorophenyl)-1H-pyrazol-3-yloxy)ethoxy)ethyl)piperidine 1) Scheme 1C-Step 1. Synthesis of 3-(2-(2-bromoethoxy)ethoxy)-1-(3,4-dichlorophenyl)-1H-pyrazole

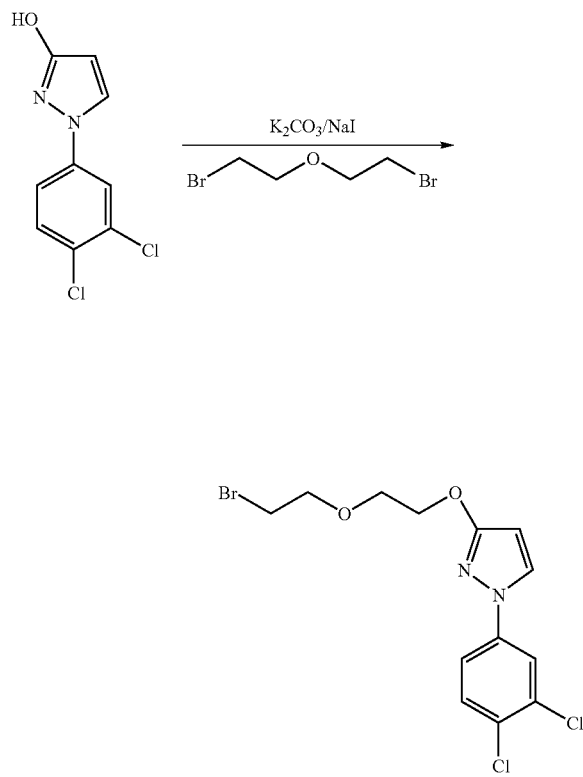

A mixture of 1-(3,4-dichlorophenyl)-1H-pyrazol-3-ol (229 mg, 1 mmol; compound prepared in the same way as Example 1, Scheme 1-step 1B), 1-bromo-2-(2-bromoethoxy)ethane (515 mg, 2 mmol), potassium carbonate (0.42 g, 3 mmol) and sodium iodide (0.15 g, 1 mmol) in dimethylformamide (12 ml) was stirred, under dry nitrogen atmosphere, at room temperature overnight. The inorganic solid was filtered off and solvent was evaporated to dryness in vacuo. The remaining residue was partitioned between water and ethyl ether. The combined organic phases were washed with water and dried over sodium sulphate, filtered and evaporated in vacuo. The residue was stirred with petroleum ether at 45° C. and decanted for 3 times to yield, after drying, 466 mg of 3-(2-(2-bromoethoxy)ethoxy)-1-(3,4-dichlorophenyl)-1H-pyrazole which was used without further purification in the next step of synthesis.

$^{1}$H-NMR (CDCl$_{3}$) δ ppm: 7.75 (d, J=2.2 Hz, 1H), 7.7 (d, J=2.7 Hz, 1H), 7.45 (m, 2H), 5.95 (d, J=2.7 Hz, 1H), 4.4 (t, J=4.4 Hz, 2H), 4.0-3.8 (m, 4H), 3.5 (t, J=6.4 Hz, 2H).

2) Scheme 1C-Step 2. Synthesis of 1-(2-(2-(1-(3,4-dichlorophenyl)-1H-pyrazol-3-yloxy)ethoxy)ethyl)piperidine

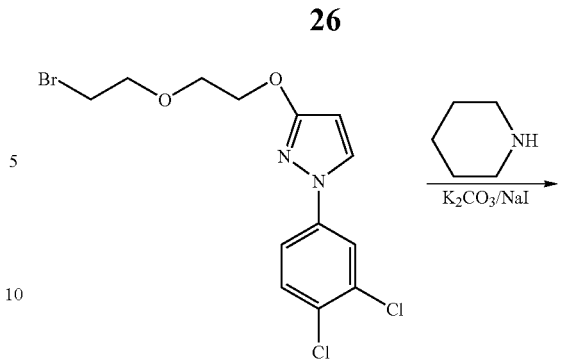

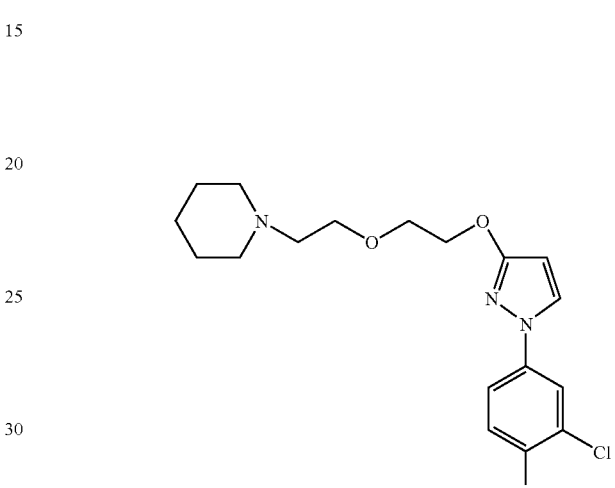

A mixture of 3-(2-(2-bromoethoxy)ethoxy)-1-(3,4-dichlorophenyl)-1H-pyrazole (0.17 mg, 0.45 mmol), piperidine (62 mg, 0.72 mmol), potassium carbonate (0.25 g, 1.8 mmol) and sodium iodide (67 mg, 0.45 mmol) in dimethylformamide (5 ml) was stirred at 100° C. overnight in a dry nitrogen atmosphere. The solvent was evaporated in vacuo and water and ethyl ether was added. The aqueous phase was extracted several times with organic solvent and the combined organic phases washed with water, dried over sodium sulphate, filtered and evaporated to dryness in vacuo. The crude dark oil obtained, 138 mg, was purified by column chromatography on silica gel (eluent: ethyl acetate/petroleum ether 2:8 to 10:0 and ethyl acetate/CH$_{3}$OH 9:1) yielding 118 mg of 1-(2-(2-(1-(3,4-dichlorophenyl)-1H-pyrazol-3-yloxy)ethoxy)ethyl)piperidine as an oil $^{1}$H-NMR (DMSO-d$_{6}$) δ ppm: 8.4 (d, J=2.6 Hz, 1H), 8.0 (d, J=2.2 Hz, 1H), 7.7 (m, 2H), 6.1 (d, J=2.6 Hz, 1H), 4.3 (t, J=4.6 Hz, 2H), 3.7 (t, J=4.6 Hz, 2H), 3.5 (t, J=6.0 Hz, 2H), 2.4 (t, J=6.0 Hz, 2H), 2.3 (m, 4H), 1.45 (m, 4H), 1.3 (m, 2H).

The salt with oxalic acid was prepared analogously to method described in Example 1, obtaining a white solid with m.p.=126-128° C.

The following example 7 was prepared with the same synthetic steps used in Example 6.

Example 7

4-(2-(2-(1-(3,4-dichlorophenyl)-1H-pyrazol-3-yloxy)ethoxy)ethyl)morpholine oxalate

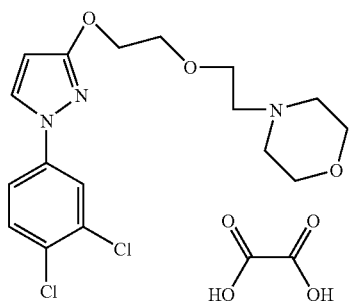

White solid. M.P.=154-156° C.

$^1$H-NMR (DMSO-$d_6$) δ ppm: 8.45 (d, J=2.6 Hz, 1H), 8.0 (d, J=2.0 Hz, 1H), 7.7 (m, 2H), 6.1 (d, J=2.6 Hz, 1H), 4.3 (t, J=4.6 Hz, 2H), 3.8-3.6 (m partially under water of solvent, 8H), 2.95 (m, 2H), 2.85 (m, 4H).

Biological Activity

Some representative compounds of the invention were tested for their activity as sigma (sigma-1 and sigma-2) inhibitors. The following protocols were followed:

Sigma-1

Brain membrane preparation and binding assays for the σ1-receptor were performed as described (DeHaven-Hudkins et al., 1992) with some modifications. In brief, guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

Each assay tube contained 10 μL of [$^3$H](+)-pentazocine (final concentration of 0.5 nM), 900 μL of the tissue suspension to a final assay volume of 1 mL and a final tissue concentration of approximately 30 mg tissue net weight/mL. Non-specific binding was defined by addition of a final concentration of 1 μM haloperidol. All tubes were incubated at 37° C. for 150 min before termination of the reaction by rapid filtration over Schleicher & Schuell GF 3362 glass fibre filters [previously soaked in a solution of 0.5% polyethylenimine for at least 1 h]. Filters were then washed with four times with 4 mL of cold Tris-HCl buffer (50 mM, pH 7.4). Following addition of scintillation cocktail, the samples were allowed to equilibrate overnight. The amount of bound radioactivity was determined by liquid scintillation spectrometry using a Wallac Winspectral 1414 liquid scintillation counter. Protein concentrations were determined by the method of Lowry et al. (1951).

Sigma-2

Binding studies for σ2-receptor were performed as described (Radesca et al., 1991) with some modifications. In brief, brains from sigma receptor type I (σ1) knockout mice were homogenized in a volume of 10 mL/g tissue net weight of ice-cold 10 mM Tris-HCl, pH 7.4, containing 320 mM sucrose (Tris-sucrose buffer) with a Potter-Elvehjem homogenizer (10 strokes at 500 r.p.m.) The homogenates were then centrifuged at 1000 g for 10 min at 4° C., and the supernatants were saved. The pellets were resuspended by vortexing in 2 mL/g ice-cold Tris-sucrose buffer and centrifuged again at 1000 g for 10 min. The combined 1000 g supernatants were centrifuged at 31000 g for 15 min at 4° C. The pellets were resuspended by vortexing in 3 mL/g 10 mM Tris-HCl, pH 7.4, and the suspension was kept at 25° C. for 15 min. Following centrifugation at 31000 g for 15 min, the pellets were resuspended by gentle Potter Elvehjem homogenization to a volume of 1.53 mL/g in 10 mM Tris-HCl pH 7.4.

The assay tubes contained 10 μL of [$^3$H]-DTG (final concentration of 3 nM), 400 μL of the tissue suspension (5.3 mL/g in 50 mM Tris-HCl, pH 8.0) to a final assay volume of 0.5 mL. Non-specific binding was defined by addition of a final concentration of 1 μM haloperidol. All tubes were incubated at 25° C. for 120 min before termination of the reaction by rapid filtration over Schleicher & Schuell GF 3362 glass fibre filters [previously soaked in a solution of 0.5% polyethylenimine for at least 1 h]. Filters were washed with three times with 5 mL volumes of cold Tris-HCl buffer (10 mM, pH 8.0). Following addition of scintillation cocktail samples were allowed to equilibrate overnight. The amount of bound radioactivity was determined by liquid scintillation spectrometry using a Wallac Winspectral 1414 liquid scintillation counter. Protein concentrations were determined by the method of Lowry et al. (1951).

References

DeHaven-Hudkins, D. L., L. C. Fleissner, and F. Y. Ford-Rice, 1992, "Characterization of the binding of [$^3$H](+)pentazocine to σ recognition sites in guinea pig brain", Eur. J. Pharmacol. 227, 371-378.

Radesca, L., W. D. Bowen, and L. Di Paolo, B. R. de Costa, 1991, Synthesis and Receptor Binding of Enantiomeric N-Substituted cis-N-[2-(3,4-Dichlorophenyl)ethyl]-2-(1-pyrrolidinyl)cyclohexylamines as High-Affinity σ Receptor Ligands, J. Med. Chem. 34, 3065-3074.

Langa, F., Codony X., Tovar V., Lavado A., Giménez E., Cozar P., Cantero M., Dordal A., Hernandez E., Pérez R., Monroy X., Zamanillo D., Guitart X., Montoliu L I., 2003, Generation and phenotypic analysis of sigma receptor type I (Sigma1) knockout mice, European Journal of Neuroscience, Vol. 18, 2188-2196.

Lowry, O. H., N. J. Rosebrough, A. L. Farr, and R. J. Randall, 1951, Protein measurement with the Folin phenol reagent, J. Biol. Chem., 193, 265.

Some of the results obtained are shown in table (I).

TABLE I

| Example | % Binding σ1 $10^{-7}$M | % Binding σ1 $10^{-8}$M |
|---|---|---|
| 1 | 70.3 | 22.2 |
| 2 | 72.2 | 4.2 |
| 3 | 55.9 | 32.6 |
| 6 | 82.8 | 23.7 |
| 7 | 61.6 | 25.8 |

The invention claimed is:
1. Compounds of formula (I),

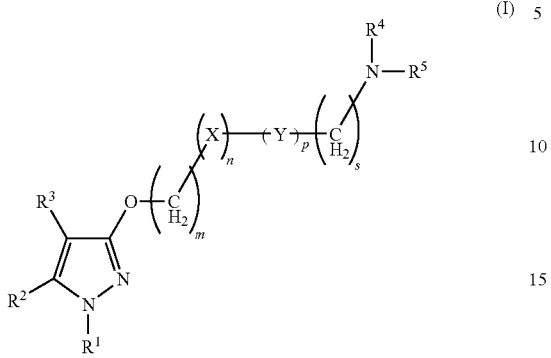

wherein
R$^1$ represents a hydrogen atom; F; Cl; Br; I; CF$_3$; OH; SH; NH$_2$; CN; an unbranched or branched, saturated or unsaturated, substituted or unsubstituted C$_{1-6}$ aliphatic group; an unbranched or branched, saturated or unsaturated, substituted or unsubstituted alkoxy radical; a saturated or unsaturated, substituted or unsubstituted, optionally at least one heteroatom as ring member containing cycloalkyl group, which may be condensed with a substituted or unsubstituted mono- or polycyclic ring system; a branched or unbranched, optionally at least one heteroatom as ring member containing alkyl-cycloalkyl group in which the cycloalkyl group is substituted or unsubstituted; a substituted or unsubstituted aryl group which may be condensed with a substituted or unsubstituted mono- or polycyclic ring system; a substituted or unsubstituted heteroaryl group which may be condensed with a substituted or unsubstituted mono- or polycyclic ring system; a branched or unbranched alkyl-aryl group in which the aryl group is substituted or unsubstituted and/or condensed with a mono- or polycyclic ring system; a branched or unbranched alkyl-heteroaryl group in which the heteroaryl group is substituted or unsubstituted and/or condensed with a mono- or polycyclic ring system; a (C=O)—R$^7$ group; a (C=O)—O—R$^8$ group; a (S=O$_2$)—R$^9$ group; or a (C=O)—NR$^{10}$R$^{11}$ group;

R$^2$ represents a hydrogen atom; F; Cl; Br; I; CF$_3$; OH; SH; NH$_2$; CN; an unbranched or branched, saturated or unsaturated, substituted or unsubstituted aliphatic group; an unbranched or branched, saturated or unsaturated, substituted or unsubstituted alkoxy radical; a saturated or unsaturated, substituted or unsubstituted, optionally at least one heteroatom as ring member containing cycloalkyl group, which may be condensed with a substituted or unsubstituted mono- or polycyclic ring system; a branched or unbranched, optionally at least one heteroatom as ring member containing alkyl-cycloalkyl group in which the cycloalkyl group is substituted or unsubstituted; a substituted or unsubstituted aryl group which may be condensed with a substituted or unsubstituted mono- or polycyclic ring system; a substituted or unsubstituted heteroaryl group which may be condensed with a substituted or unsubstituted mono- or polycyclic ring system; a branched or unbranched alkyl-aryl group in which the aryl group is substituted or unsubstituted and/or condensed with a mono- or polycyclic ring system; a branched or unbranched alkyl-heteroaryl group in which the heteroaryl group is substituted or unsubstituted and/or condensed with a mono- or polycyclic ring system; a (C=O)—R$^7$ group; a (C=O)—O—R$^8$ group; a (S=O)—R$^9$ group; or a (C=O)—NR$^{10}$R$^{11}$ group;

R$^3$ is hydrogen;

R$^4$ and R$^5$ form together with the bridging nitrogen atom a substituted or unsubstituted heterocyclyl group which is optionally condensed with a substituted or unsubstituted mono- or polycyclic ring system;

X represents an oxygen atom; a CH—R$^{12}$ group with R$^{12}$ being a —CH$_3$, SH, OH, NH$_2$, CF$_3$ group; Cl, F, Br, I, or CN;

Y represents a (S=O$_2$) group;

m is selected from 1, 2, 3 or 4;

n is selected from 0 or 1;

p is selected from 0 or 1;

s is selected from 1, 2, 3 or 4;

and n plus p is 1;

R$^7$, R$^8$, R$^9$, R$^{10}$ and R$^{11}$, identical or different, represent a hydrogen atom; an unbranched or branched, saturated or unsaturated, substituted or unsubstituted C$_{1-6}$ aliphatic group; a branched or unbranched, substituted or unsubstituted C$_{1-6}$ alkoxy radical; a saturated or unsaturated, substituted or unsubstituted, optionally at least one heteroatom as ring member containing cycloalkyl group; a branched or unbranched, substituted or unsubstituted, optionally at least one heteroatom as ring member containing C$_{1-6}$ alkyl-cycloalkyl group; a substituted or unsubstituted aryl group; a substituted or unsubstituted heteroaryl group; a branched or unbranched, substituted or unsubstituted C$_{1-6}$ alkyl-aryl; a branched or unbranched, substituted or unsubstituted C$_{1-6}$ alkyl-heteroaryl group;

optionally in form of one of the stereoisomers, a racemate or in form of a mixture of at least two of the stereoisomers, in any mixing ratio, or a corresponding salt thereof.

2. The compounds according to claim 1, characterized in that R$^1$ represent a hydrogen atom; F; Cl; Br; I; CF$_3$; OH; SH; NH$_2$; CN; an unbranched or branched C$_{1-6}$ alkyl group which is substituted or unsubstituted with substituents independently selected from the group consisting of F, Cl, Br, I, NH$_2$, SH, OH, SO$_2$, or CF$_3$; an unbranched or branched, alkoxy radical which is optionally substituted with substituents independently selected from the group consisting of F, Cl, Br, I, NH$_2$, SH, OH, SO$_2$, or CF$_3$; a saturated or unsaturated, optionally at least one heteroatom as ring member containing cycloalkyl group which is substituted or unsubstituted with substituents independently selected from the group consisting of F, Cl, Br, I, NH$_2$, SH, OH, SO$_2$, or CF$_3$; a branched or unbranched, optionally at least one heteroatom as ring member containing alkyl-cycloalkyl group in which the cycloalkyl group is substituted or unsubstituted with substituents independently selected from the group consisting of F, Cl, Br, I, NH$_2$, SH, OH, SO$_2$, or CF$_3$; an aryl group which is substituted or unsubstituted with substituents independently selected from the group consisting of F, Cl, Br, I, NH$_2$, SH, OH, SO$_2$, or CF$_3$; a heteroaryl group which is substituted or unsubstituted with substituents independently selected from the group consisting of F, Cl, Br, I, NH$_2$, SH, OH, SO$_2$, or CF$_3$; a branched or unbranched alkyl-aryl group which is substituted or unsubstituted with substituents independently selected from the group consisting of F, Cl, Br, I, NH$_2$, SH, OH, SO$_2$, or CF$_3$; a branched or unbranched alkyl-heteroaryl group which is substituted or unsubstituted with substituents independently selected from the group consisting of F, Cl, Br, I, $NH_2$, SH, OH, $SO_2$, or $CF_3$.

3. The compounds according to claim 1, characterized in that $R^2$ represents a hydrogen atom; F; Cl; Br; I; $CF_3$; OH; SH; $NH_2$; CN; an unbranched or branched $C_{1-6}$ alkyl group which is substituted or unsubstituted with substituents independently selected from the group consisting of F, Cl, Br, I, $NH_2$, SH, OH, $SO_2$, or $CF_3$; an unbranched or branched, alkoxy radical which is optionally substituted with substituents independently selected from the group consisting of F, Cl, Br, I, $NH_2$, SH, OH, $SO_2$, or $CF_3$; a saturated or unsaturated, optionally at least one heteroatom as ring member containing cycloalkyl group which is substituted or unsubstituted with substituents independently selected from the group consisting of F, Cl, Br, I, $NH_2$, SH, OH, $SO_2$, or $CF_3$; a branched or unbranched, optionally at least one heteroatom as ring member containing alkyl-cycloalkyl group in which the cycloalkyl group is substituted or unsubstituted with substituents independently selected from the group consisting of F, Cl, Br, I, $NH_2$, SH, OH, $SO_2$, or $CF_3$; an aryl group which is substituted or unsubstituted with substituents independently selected from the group consisting of F, Cl, Br, I, $NH_2$, SH, OH, $SO_2$, or $CF_3$; a heteroaryl group which is substituted or unsubstituted with substituents independently selected from the group consisting of F, Cl, Br, I, $NH_2$, SH, OH, $SO_2$, or $CF_3$; a branched or unbranched alkyl-aryl group which is substituted or unsubstituted with substituents independently selected from the group consisting of F, Cl, Br, I, $NH_2$, SH, OH, $SO_2$, or $CF_3$; a branched or unbranched alkyl-heteroaryl group which is substituted or unsubstituted with substituents independently selected from the group consisting of F, Cl, Br, I, $NH_2$, SH, OH, $SO_2$, or $CF_3$.

4. The compounds according to claim 1, characterized in that $R^4$ and $R^5$ form together with the bridging nitrogen atom a substituted or unsubstituted, at least one heteroatom as ring member containing cycloalkyl group.

5. The compounds according to claim 1, characterized in that $R^1$ represents a hydrogen atom; F; Cl; Br; I; $CF_3$; OH; SH; $NH_2$; CN; an optionally, at least mono-substituted ethyl, propyl, n-propyl, i-propyl, tert-butyl, n-butyl, i-butyl, cyclohexyl, phenyl, benzyl, phenethyl or naphtyl group with substituents independently selected from the group consisting of F, Cl, Br, I, $NH_2$, SH, OH, $SO_2$, or $CF_3$;

$R^2$ represents a hydrogen atom; an unbranched or branched, $C_{1-6}$ alkyl group which is substituted or unsubstituted with substituents independently selected from the group consisting of F, Cl, Br, I, $NH_2$, SH, OH, $SO_2$, or $CF_3$; a branched or unbranched alkyl-aryl group selected from the group consisting of benzyl or phenethyl which is substituted or unsubstituted with substituents independently selected from the group consisting of F, Cl, Br, I, $NH_2$, SH, OH, $SO_2$, or $CF_3$; a branched or unbranched alkyl-heteroaryl group which is substituted or unsubstituted with substituents independently selected from the group consisting of F, Cl, Br, I, $NH_2$, SH, OH, $SO_2$, or $CF_3$;

$R^3$ represents a hydrogen atom;

$R^4$ and $R^5$ form together with the bridging nitrogen atom a substituted or unsubstituted, piperidine, morpholine, pyrrolidine or piperazine group which is substituted or unsubstituted with substituents independently selected from the group consisting of F, Cl, Br, I, $NH_2$, SH, OH, $SO_2$, or $CF_3$;

X represents an oxygen atom or a CH—$R^{12}$ group with $R^{12}$ being OH;

Y represents a (S=$O_2$) group;

m is selected from 1 or 2;

n is selected from 0 or 1;

p is selected from 0 or 1;

s is selected from 1 or 2;

and n plus p is 1;

optionally in form of one of the stereoisomers, a racemate or in form of a mixture of at least two of the stereoisomers, in any mixing ratio, or a corresponding salt thereof.

6. The compounds according to claim 1, characterized in that m is selected from 1 or 2.

7. The compounds according to claim 1, characterized in that n is 1.

8. The compounds according to claim 1, characterized in that p is 0.

9. The compounds according to claim 1, characterized in that s is selected from 1 or 2.

10. The compounds according to claim 1, characterized in that $R^4$ and $R^5$ form together with the bridging nitrogen atom a substituted or unsubstituted 5- or 6-membered ring selected from the group consisting of pyrrolidine, morpholine, piperidine or piperazine.

11. The compounds according to claim 1, characterized in that n is selected from 1 and X represents an oxygen atom; a CH—$R^{12}$ group with $R^{12}$ being —$CH_3$, SH, OH, $NH_2$, $CF_3$ group; Cl, F, Br, I, or CN.

12. The compounds according to claim 1, characterized in that n is selected from 1 and X represents an oxygen atom or a CH—OH group.

13. The compounds according to claim 1, wherein the compound is selected form the group consisting:

1-(1-(3,4-dichlorophenyl)-1H-pyrazol-3-yloxy)-3-morpholinopropan-2-ol, 1-(1-(3,4-dichlorophenyl)-1H-pyrazol-3-yloxy)-3-(piperidin-1-yl)propan-2-ol, 1-(1-(3,4-dichlorophenyl)-1H-pyrazol-3-yloxy)-3-(pyrrolidin-1-yl)propan-2-ol, 1-(1-(3,4-dichlorophenyl)-1H-pyrazol-3-yloxy)-3-(4-methylpiperazin-1-yl)propan-2-ol, 2-(1-(3,4-dichlorophenyl)-1H-pyrazol-3-yloxy)ethyl 2-morpholino ethane sulfonate, 1-(2-(2-(1-(3,4-dichlorophenyl)-1H-pyrazol-3-yloxy) ethoxy)ethyl) piperidine, and 4-(2-(2-(1-(3,4-dichlorophenyl)-1H-pyrazol-3-yloxy) ethoxy)ethyl)morpholine, or any acceptable salt thereof.

14. A process for the preparation of compounds of formula (I) by reacting compounds of general formula (II)

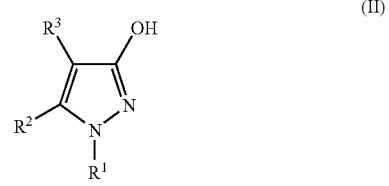

in which R¹, R² and R³ have the meaning according to claim 1, with a compound of formula (III):

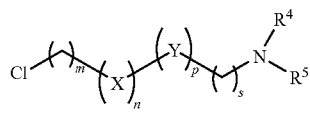
(III)

in which R⁴, R⁵, X, Y, m, n, p, and s are defined according to claim 1.

15. A process for the preparation of compounds of formula (I) by reacting compounds of general formula (II)

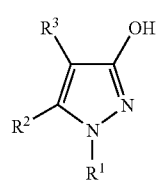
(II)

in which R¹, R² and R³ have the meaning according to claim 1, with a compound of formula (IV),

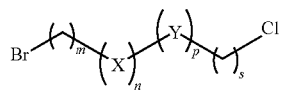
(IV)

in which X, Y, m, n, p, and s have the meaning according to claim 1; optionally followed by reacting with an amine with general formula (V),

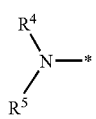
(V)

wherein R⁴ and R⁵ have the meaning according to claim 1.

16. A medicament comprising at least one compound of formula (I), according to claim 1, said compound being optionally in form of one of the stereoisomers, a racemate or in form of a mixture of at least two of the stereoisomers, in any mixing ratio, or a corresponding salt thereof.

17. Process of manufacture of a medicament comprising a compound of formula (I) according to claim 1, wherein the process comprises at least the step of formulating the compound into tablets, pellets, capsules, lozenges, aqueous or oily solutions, suspensions, emulsions, suppositories or dry powdered forms suitable for reconstitution with water or other suitable liquid medium before use, for immediate or retarded release.

18. A method for the treatment of a sigma receptor-mediated disease or condition, said method comprising administering a compound of formula (I) according to claim 1, wherein the disease is pain, wherein the pain is allodynia and/or hyperalgesia.

19. The compounds according to claim 1, characterized in that they are in the form of one of the enantiomers or diastereomers, or in the form of a mixture of at least two of the enantiomers and/or diastereomers, in any mixing ratio.

20. The compounds according to claim 5, characterized in that they are in the form of one of the enantiomers or diastereomers, or in the form of a mixture of at least two of the enantiomers and/or diastereomers, in any mixing ratio.

21. The compounds according to claim 10, characterized in that the substituted or unsubstituted 5- or 6-membered ring is morpholine, pyrrolidine, or piperidine.

22. The compounds according to claim 16, characterized in that they are in the form of one of the enantiomers or diastereomers, or in the form of a mixture of at least two of the enantiomers and/or diastereomers, in any mixing ratio.

* * * * *